US011697032B2

(12) United States Patent
Sampayan et al.

(10) Patent No.: US 11,697,032 B2
(45) Date of Patent: *Jul. 11, 2023

(54) FLASH RADIOTHERAPY ACCELERATOR

(71) Applicants: Lawrence Livermore National Security, LLC, Livermore, CA (US); Opcondys, Inc., Manteca, CA (US)

(72) Inventors: Stephen E. Sampayan, Manteca, CA (US); Kristin Cortella Sampayan, Manteca, CA (US); George James Caporaso, East Quogue, NY (US); Yu-Jiuan Chen, Fremont, CA (US); Clifford C. Shang, Livermore, CA (US)

(73) Assignees: LAWRENCE LIVERMORE NATIONAL SECURITY, LLC, Livermore, CA (US); OPCONDYS, INC., Manteca, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/559,776

(22) Filed: Dec. 22, 2021

(65) Prior Publication Data
US 2022/0203135 A1 Jun. 30, 2022

Related U.S. Application Data

(60) Provisional application No. 63/131,315, filed on Dec. 29, 2020.

(51) Int. Cl.
*A61N 5/10* (2006.01)
(52) U.S. Cl.
CPC ......... *A61N 5/1071* (2013.01); *A61N 5/1067* (2013.01); *A61N 5/1077* (2013.01)

(58) Field of Classification Search
CPC ...... A61N 5/10–1084; A61N 2005/1085–1098
See application file for complete search history.

(56) References Cited

U.S. PATENT DOCUMENTS 2,331,788 A 10/1943 Baldwin
4,646,027 A 2/1987 Birx et al.
(Continued)

FOREIGN PATENT DOCUMENTS

| KR | 1020200038429 | 4/2020 |
| WO | 2019059932 A1 | 3/2019 |
| WO | 2022/155315 A1 | 7/2022 |

OTHER PUBLICATIONS

International Search Report and Written Opinion dated Jun. 2, 2022 for International Patent Application No. PCT/US2021/065016.
(Continued)

*Primary Examiner* — Thaddeus B Cox
(74) *Attorney, Agent, or Firm* — Perkins Coie LLP

(57) ABSTRACT

Methods, devices and systems for ultra-high dose radiotherapy are disclosed. The described techniques rely in-part on active switching control of a photoconductive switch during the time the accelerator is accelerating charged particles to produce the output radiation at the desired dose rates. One flash radiotherapy system includes an induction accelerator, and a controllable switch coupled to the induction accelerator. The switch is operable to produce a plurality of voltage pulses to drive the induction accelerator. The radiotherapy system also includes a radiation measurement device to measure output radiation produced by the radiotherapy system and provide feedback to the controllable switch. The controllable switch is operable to, based on the received feedback, modify an amplitude, shape, spacing, number or width of the voltage pulses that are supplied to the particle accelerator to deliver the desired output radiation.

15 Claims, 7 Drawing Sheets

(56) References Cited

U.S. PATENT DOCUMENTS

| | | |
|---|---|---|
| 4,888,556 A | 12/1989 | Buttram et al. |
| 6,066,901 A | 5/2000 | Burkhart et al. |
| 7,710,051 B2 | 5/2010 | Caporaso et al. |
| 10,270,368 B2 | 4/2019 | Sampayan |
| 10,282,567 B2 | 5/2019 | Miller et al. |
| 10,792,517 B2 | 10/2020 | Lee et al. |
| 2007/0228301 A1 | 10/2007 | Nakano |
| 2009/0224700 A1 | 9/2009 | Chen et al. |
| 2010/0032580 A1 | 2/2010 | Caporaso et al. |
| 2010/0102246 A1 | 4/2010 | Park et al. |
| 2013/0140468 A1 | 6/2013 | Chen |
| 2014/0368108 A1* | 12/2014 | Nahum ............... G21B 3/006 315/10 |
| 2014/0371511 A1 | 12/2014 | Zwart et al. |
| 2016/0287905 A1 | 10/2016 | Liger |
| 2018/0161595 A1 | 6/2018 | Fuentes |
| 2022/0219014 A1 | 7/2022 | Sampayan et al. |

OTHER PUBLICATIONS

Feder, T., "High radiation dose rates may improve cancer therapy," Physics Today, 73, 12, 24 (2020); doi: 10.1063/PT.3.4631, 4 pages.

Maxim, P., G., et al., "Flash radiotherapy: Newsflash or flash in the pan?" Med. Phys. 46 (10), Oct. 2019, American Association of Physicists in Medicine, 5 pages.

Maxim, P., G., et al., "Phaser: A platform for clinical translation of Flash cancer radiotherapy," Radiotherapy and Oncology 139 (2019) 28-33, Elsevier, 6 pages.

J. Barnard, et al., "Induction accelerator architectures for heavy-ion fusion," Nucl. Instr. Meth, in Phys. Res. A, vol. 415, No. 1-2, pp. 218-228, 1998. LLNS Proprietary Information IL-13640 1/.

S. Sampayan, P. Vitello, M. Krogh and J. Elizondo, "Multilayer ultra-high gradient insulator technology," in 18th International Symposium on Discharges and Electrical Insulation in Vacuum, Eindhoven, Netherlands, 1998.

A. Fateev, G. Dolbilov, I. Ivanov, V. Kosukhin, N. Lebedev, V. Petrov, V. Razuvakin, V. Shvetsov and M. Yurkov, "Status of the first stage of linear induction accelerator SILUND-21," in Proceedings Particle Accelerator Conference, Dallas, TX USA, 1995.

A. Toepfer, "A review of accelerator concepts for the advanced hydrotest facility," in 19th International Linear Accelerator Conference, Chicago, IL, 1998.

B. Kulke and R. Kihara, "Recent Performance Improvements on FXR," IEEE Trans. Nucl. Sci., vol. 30, No. 4, pp. 3030-3032, 1983.

C. Karzmark, "Advances is linear accelerator design for radiotherapy," Med. Phys., vol. 11, No. 2, pp. 105-128, 1984.

C. Shang, Y.-J. Chen, G. Caporaso, T. Houck, N. Molau, S. Nelson, W. Ng and J. Fockler, "BBU design of linear induction accelerator cells for radiography application," in 1997 Particle Accelerator Conference, Vancouver, BC Canada, 1997.

D. Birx, "Induction linear accelerators," AIP Conference Proceedings, vol. 249, pp. 1553-1614, 1992.

E. Ginzton, W. Hansen and W. Kennedy, "A linear electron accelerator," Rev. Sc. Instr., vol. 19, pp. 89-108, 1948.

E. Merle, R. Boivinet, M. Mouillet, O. Pierret, P. Anthouard, J. Bardy, C. Bonnafond, A. Devin, P. Eyl and C. Vermare, "Installation of the AIRIX Induction Accelerator," in 19th International Linear Accelerator Conference, Chicago, IL USA, 1998.

E. Schuler, et al., "Experimental Platform for Ultra-high Dose Rate Flash Irradiation of Small Animals Using a Clinical Linear Accelerator," Int J of Rad Oncology Biol Phys, vol. 97, No. 1, pp. 195-203, 2017.

G. Becker and D. Caswell, "Operation of a six-MeV linear accelerator," Rev. Sci. Instr., vol. 22, No. 6, pp. 402-405, 1951.

G. Caporaso, et al., "A compact linac for intensity modulated proton therapy based on a dielectric wall accelerator," Physica Medica, vol. 24, No. 2, pp. 98-101, 2008.

G. R. Neil, J. Edighoffer, P. Livingston, J. Rawls and I. Smith, "The induction-FEL design for the White Sands missile range," Nucl. Instr. Meth. Phys. Res. A, vol. 296, No. 1-3, pp. 257-262, 1990.

H. Kirbie, B. Hickman, B. Lee, C. Ollis, C. Brooksby and R. Saethre, "An all solid state pulse power source for high PRF induction accelerators," in 23rd International Power Modulator Symposium, Rancho Mirage, CA USA, 1998.

H. Kirbie, G. Caporaso, D. Goerz, R. Hanks, B. Hickman, B. Lee, C. Brooksby and R. Saethre, "MHz repetition rate solid-state driver for high current induction accelerators," in 1999 Particle Accelerator Conference, New York, NY USA, 1999.

I. Smith, "Induction voltage adders and the induction accelerator family," Phys. Rev. ST Accel. Beams, vol. 7, pp. 064801-1-40, 2004.

I. Uetomi, M. Yamazaki, H. Kobayashi and I. Sato, "Extended Theory of Beam Loading in Electron Linac," Jpn. J. Appl. Phys., vol. 32, No. 6A, pp. 2858-2864, 1993.

International Search Report and Written Opinion for International Patent Application No. PCT/US2022/012288 dated May 4, 2022 (10 pages).

J. A. Watson, A. N. Payne, S. E. Sampayan and C. W. Ollis, "Precision voltage regulation on the 5 KHz, 3.125 MW ETA-II pulsed power system," in Eighth IEEE International Conference on Pulsed Power, San Diego, CA, USA, 1991.

J. Barnard, R. Bangerter, A. Faltens, T. Fessenden, A. Friedman, E. Lee, B. Logan, S. Lund, W. Meier, W. Sharp and S. Yu,, "Induction accelerator architectures for heavy-ion fusion," Nucl. Instr. Meth, in Phys. Res. A, vol. 415, No. 1-2, pp. 218-228, 1998.

J. Beal, N. Christofilos and R. Hester, "The Astron Linear Accelerator," IEEE Trans. Nucl. Sci., vol. 16, No. 3, pp. 294-298, 1969.

J. Bourhis, et al., "Treatment of a first patient with Flash-radiotherapy," Radiotherapy and Oncology, vol. 139, pp. 18-22, 2019.

J. D. Wilson, E. M. Hammond, G. S. Higgins and K. Petersson, "Ultra-High Dose Rate (Flash) Radiotherapy: Silver Bullet or Fool's Gold?," Front. Oncology, vol. 9, p. 1563, 2020.

J. Deng, B. Ding, J. Shi, Y. He, J. Li, Q. Li, G. Cao, L. Wen and G. Dai, "Upgrading of Linear Induction Accelerator X-Ray Facility (LIAXF)," in 19th International Linear Accelerator Conference, Chicago, IL USA, 1998.

J. Deng, et al., "Design of the Dragon-I Linear Induction Accelerator," in 21st International Linear Accelerator Conference, Gyeongju, Korea, 2002.

J. Melton and E. Rose, "A model for the magnetic cores of linear induction accelerator cells," in Tenth IEEE International Pulsed Power Conference, Albuquerque, NM USA, 1995.

J. Smith, V. Bailey, H. Lackner and S. Putnam, "Performance of the spiral line induction accelerator," in Proceedings of the 1997 Particle Accelerator Conference, Vancouver, BC Canada, 1997.

J. Weir, J. Boyd, Y.-J. Chen, J. Clark, D. Lager and A. Paul, "Improved ETA-II accelerator performance," in Proceedings of the 1999 Particle Accelerator Conference, New York, NY USA, 1999.

K. Brown, "Properties of iris-loaded guides," in Conference on Linear Accelerators, Upton, NY, 1961.

K. Sampayan and S. Sampayan, "Wide Bandgap Photoconductive Switches Driven by Laser Diodes as a High-Voltage Mosfet Replacement for Bioelectrics and Accelerator Applications," in IEEE Pulsed Power & Plasma Science, Orlando, FL USA, 2019.

K. Takayama and R. J. Briggs, Induction Accelerators, New York: Springer, 2011.

K. Yatsui, et al., "Pulse-power technology and its applications at LBT, Nagaoka," in 11th International Conference on High-Power Particle Beams, Prague, Czech Republic, 1996.

L. Reginato, "The Advanced Test Accelerator (ATA), a 50-MeV 10-kA Induction Linac," IEEE Trans. Nucl. Sci., vol. 30, pp. 2970-2974, 1983.

L. Yang, L. Yang, F. Yang and X. Ma, "Slow-Scale and Fast-Scale instabilities in parallel-connected single-phase H-bridge inverters: A design-oriented study," Int. J. Bifurcation and Chaos, vol. 30, No. 1, pp. 2050005-1-20, 2020.

M. Burns, et al., "DAHRT accelerators update and plans for initial operation," in Particle Accelerator Conference, New York, NY USA, 1999.

M. Burns, et al., "Status of the DARHT phase 2 long-pulse accelerator," in 2001 Particle Accelerator Conference, Chicago, IL USA, 2001.

(56) References Cited

OTHER PUBLICATIONS

M. Hodgdon, "Mathematical theory and calculations of magnetic hysteresis curves," IEEE Trans. Magnetics, vol. 24, No. 6, pp. 3120-3122, 1988.

M. Jaccard, et al., "High dose-per-pulse electron beam dosimetry: Commissioning of the Oriatron eRT6 prototype linear accelerator for preclinical use," Med. phys., vol. 45, No. 2, p. 863-874, 2018.

M.-C. Vozenin, et al., "The Advantage of Flash Radiotherapy Confirmed in Mini-pig and Cat-cancer Patients," Clin Cancer Res, vol. 25, No. 1, pp. 35-42, 2019.

N. Christofilos, R. Hester, W. Lamb, D. Reagan, W. Sherwood and R. Wright, "High current linear induction accelerator for electrons," Rev. Sci. Instr., vol. 35, No. 7, pp. 886-890, 1964.

N. Khizhnyak, V. Tolok, V. Chechkin and N. Nazarov, "The acceleratiom of large current pulses in electron linear accelerators," Plasma Physics (J. Nucl. Ener. C), vol. 4, pp. 129-134, 1962.

O. Zlobinskaya, et al., "The Effects of Ultra-High Dose Rate Proton Irradiation on Growth Delay in the Treatment of Human Tumor Xenografts in Nude Mice," Radiat. Res., vol. 181, No. 2, pp. 177-183, 2014.

P. Anthouard, et al., "Airix at CESTA," in 11th International Conference on High-Power Particle Beams, Prague, Czech Republic, 1996.

P. Corcoran, et al., "Experimental tests of the power supply and prototype cell for the 1.5 MeV SLIA acceleration unit," in 1991 IEEE Particle Accelerator Conference, San Francisco, CA USA, 1991.

P. G. Maxim, P. Keall and J. Cai, "Point/Counterpoint, Flash radiotherapy: Newsflash or flash in the pan?," Med. Phys., vol. 46, No. 10, pp. 4287-4290, 2019.

P. Montay-Gruel, et al., "Irradiation in a flash: Unique sparing of memory in mice after whole brain irradiation with dose rates above 100 Gy/s," Radiotherapy and Oncology, vol. 124, No. 3, pp. 365-369, 2017.

P. Seidl, et al., "Irradiation of materials with short, intense ion pulses at NDCX-II," Laser and Part. Beams, vol. 35, No. 2, pp. 373-378, 2017.

R. Cassel, M. Nguyen, E. Cook and C. Brooksby, "A hybrid solid state induction modulator for klystrons," in 16th IEEE International Pulsed Power Conference, Albuquerque, NM USA, 2007.

R. J. Adler, "Pulse Power Formulary," Air Force Office of Scientific Research, Washington, DC USA, 1989.

R. Neal, "Design of linear electron accelerators with beam loading," J. Appl. Phys., vol. 26, No. 7, pp. 1019-1024, 1958.

R. Post and N. Shiren, "The Stanford Mark II Inear accelerator," Rev. Sci. Instr., vol. 26, No. 2, pp. 205-209, 1955.

R. Wideröe, "Über ein neues Prinzip zur Herstellung hoher Spannungen," Archiv für Elektrotechnik, vol. 21, No. 4, p. 387-406, 1928.

S. Allen, et al., "Generation of high power 140 GHz microwaves with an FEL for the MTX experiment," in Proceedings of International Conference on Particle Accelerators, Washington, DC USA, 1993.

S. Benedetti, A. Grudiev and A. Latina, "High gradient linac for proton therapy," Physical Rev. Accel. Beams, vol. 20, pp. 040101-1-19, 2017.

S. Humphries, Principals of Charged Partice Acceleration, Hoboken, NJ: John Wiley and Sons, 1999.

S. Mazumder, "Stability analysis of parallel DC-DC converters," IEEE Trans. Aerospace Electr. Syst., vol. 42, No. 1, pp. 50-69, 2006.

S. Sampayan, et al., "Characterization of carrier behavior in photonically excited 6H silicon carbide exhibiting fast, high voltage, bulk transconductance properties," Scientific Reports, 2021.

S. Sampayan, et al., "Performance characteristics of an induction linac magnetic pulse compression modulator at multi-kilohertz pulse repetition frequencies," in IEEE Particle Accelerator Conference, San Francisco, CA USA, 1991.

S. Sampayan, G. Caporaso, Y.-J. Chen, D. Decker and W. Turner, "Energy sweep compensation of induction accelerators," in 1990 LINAC Conference, Albuquerque, NM USA, 1990.

S. Sampayan, P. Vitello, M. Krogh and J. Elizondo, "Multilayer high gradient insulator technology," IEEE Trans. Dielect. Elect. Insul., vol. 7, No. 3, pp. 334-339, 2000.

T. Feder, "High radiation dose rates may improve cancer therapy," Physics today, vol. 73, No. 12, pp. 24-26, 2020.

T. Houck, et al., "Measured and theoretical characterization of the RF properties of stacked, high-gradient insulator material," in Proceedings of the 1997 Particle Accelerator Conference, Vancouver, BC Canada, 1997.

T. Mackie, T. Holmes, S. Swerdloff, P. Reckwerdt, J. Deasy, J. Yang, B. Paliwal and T. Kinsella, "Tomotherapy: A new concept for the delivery of dynamic conformal radiotherapy," Med. Phys., vol. 20, pp. 1709-1719, May 31, 1993.

V. Smirnov and S. Vorozhtsov, "Modern compact accelerators of cyclotron type for medical applications," Phys. Part. Nuclei, vol. 47, p. 863-883, 2016.

W. Panofsky and M. Bander, "Asymptotic theory of beam break-up in linear accelerators," Re. Sci. Instr., vol. 39, No. 2, pp. 206-212, 1968.

W. Turner, G. Caporaso, G. Craig, J. DeFord, L. Reginato, S. Sampayan, R. Kuenning and I. Smith, "Impedance characteristics of induction accelerator cells," in International Conference on High-Power Particle Beams, Karlsruhe, Germany, 1988.

W. Waldron, et al., "The NDCX-II engineering design," Nucl. Instr. Meth. Phys. Res. A, vol. 733, pp. 226-232, 2014.

W. Waldron, J. Galvin, W. Ghiorso and C. Pappas, "The design and testing of an inductive voltage adder for ALS-U kicker magnets," in IEEE International Power Modulator and High Voltage Conference, San Francisco, CA USA, 2016.

Y.-J. Chen, et al., "Compact Dielectric Wall Accelerator Development For Intensity Modulated Proton Therapy And Homeland Security Applications," in 10th International Conference on Applications of Nuclear Techniques, Crete, Greece, 2009.

\* cited by examiner

FLASH RADIOTHERAPY ACCELERATOR

CROSS-REFERENCE TO RELATED APPLICATIONS

This patent document claims priority to and benefits of U.S. Provisional Patent Application No. 63/131,315 entitled "FLASH RADIOTHERAPY ACCELERATOR," filed on Dec. 29, 2020. The entire contents of the before-mentioned patent applications are incorporated by reference as part of the disclosure of this patent document.

STATEMENT REGARDING FEDERALLY SPONSORED RESEARCH OR DEVELOPMENT

This invention was made with Government support under Contract No. DE-AC52-07NA27344 awarded by the United States Department of Energy. The Government has certain rights in the invention.

TECHNICAL FIELD

This document relates to FLASH radiotherapy systems and in particular to FLASH radiotherapy systems that use a charged particle accelerator.

BACKGROUND

Recent studies indicate that intense pulsed radiation at high dose rates for cancer therapy has better efficacy and is less damaging to healthy tissue than lower radiation dose given over a longer period of time. This approach involves ultra-high does rate radiotherapy and sometimes referred to as "FLASH" radiotherapy. Although the mechanisms are not clearly understood, FLASH radiotherapy is hypothesized to provide better efficacy due to hypoxic effects. The response of tumors appears to be independent of dose rate but healthy tissue seems to gain protection from radiation damage by the reduced production of free radicals during a momentary high dose rate pulse. Research to date indicates these protective effects within healthy tissue become even more pronounced at dose rates above 100 Grays per second (Gy/s). This technique requires controlling not only the total dose, but also the dose rate. Therefore, there is a need to control and deliver such radiotherapy dose rate.

SUMMARY

The disclosed embodiments relate to methods, devices and systems that address the shortcomings of the existing radiotherapy systems and, among other features and benefits, enable FLASH radiotherapy via delivery of radiation with high dose rates in a controllable fashion using an accelerator. The disclosed techniques rely in-part on active switching control during the time the accelerator is accelerating charged particles to produce the radiation.

One aspect of the disclosed embodiments relates to a FLASH radiotherapy system that includes an induction accelerator, and a controllable switch coupled to the induction accelerator and operable to produce a plurality of voltage pulses to drive the induction accelerator. The FLASH radiotherapy system also includes a radiation measurement device configured to measure output radiation produced by the radiotherapy system and provide feedback to the controllable switch. The controllable switch is operable to modify the plurality of voltage pulses based on the feedback from the radiation measurement device.

DETAILED DESCRIPTION

Figure 1:
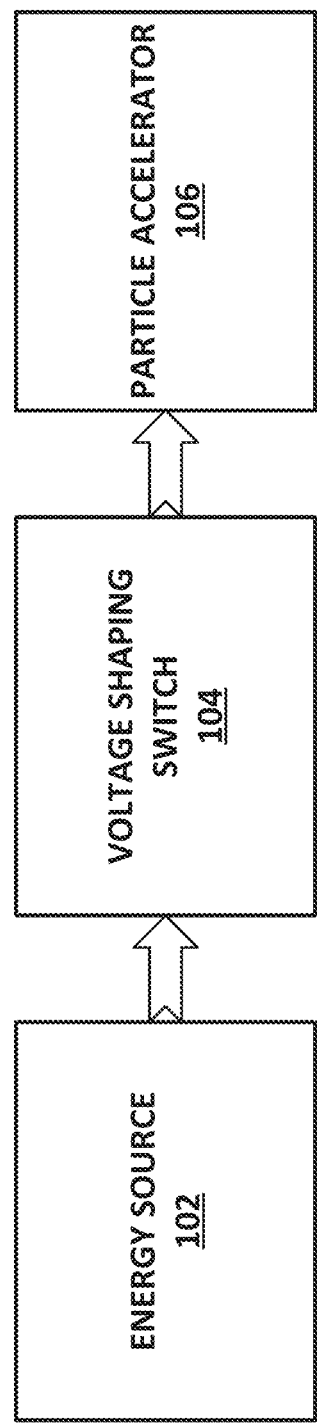
FIG. 1 is a block diagram of a particle accelerator system for radiotherapy applications in accordance with an example embodiment.

Much of the work in FLASH radiotherapy to date uses modified radio frequency accelerators. These systems produce individual micro pulses of charged particles that average to a net dose rate for a given total dose. Dose rate is generally controlled by adjusting the spacing between micro pulses. The details are as follows. These particular types of electron accelerators rely on the injection of high peak power RF energy into slow wave iris loaded waveguide structures. Although the acceleration gradients can be significant, significant power is also required. For instance, a 3-m long system achieving 30 MeV requires 12.7-MW of RF power. The "fill time" of the structure at 400-mA of beam current is approximately 1 μs. Pulsed widths for some systems are approximately 5 μs and although the measured dose rate at the radiation exit window may be high, the dose rate at 1 m distance, a common treatment distance, is estimated at only 6 Gy/s. Further, at close proximity to the exit window, the high dose-rate region is quite small (approximately 2 cm radius).

To achieve the high peak powers, devices such as magnetrons or klystrons are used. The only control afforded this type of system to increase dose rate is to decrease the time between each macro-pulse, thus increasing the system duty cycle. Although thermal inertia in electronic components such as magnetrons or klystrons, power supplies, etc., may allow control of dose rate for a short time, these systems cannot be practically implemented at least because at longer time frames the elements within the system will be highly stressed, leading to premature catastrophic failure.

The distinctive feature of these aforementioned accelerators is that they use RF energy as an intermediate step to create an accelerating gradient. Charged particles in synchronization with this oscillating electric field along the accelerator gain energy while particles not in synchronization are lost. To achieve ultra-high dose rates requires large beam currents. But these currents can interact adversely with the RF energy itself and the structure to contain the RF energy. The net result is to either shorten the pulse and/or counteract the accelerating mechanism.

A simpler form of accelerator, also known as a pulsed power accelerator, directly applies a pulsed voltage across a set of electrodes so that charged particles are accelerated while the pulse is present. A salient feature of this method is that it is well known that a fast pulse can take nanoseconds to microseconds to penetrate a highly conductive wall. Thus, multiple pulsed acceleration gaps can be arranged in sequence so that one acceleration gap can function in isolation of the adjoining gap. So that with proper design, a sequential acceleration system can be realized without the necessity of creating RF energy as an inefficient intermediate step. The advantage of this type system is that it is less susceptible to the above issues even at extremely high beam currents. A specialized form of this type of pulsed power accelerator is the induction linear accelerator.

Specialized induction linear accelerators built for dynamic radiography for the US Department of Energy use a significantly different technique for generating charged particle beams with extremely high dose rates exceeding $10^6$ Gy/s at 1-m distance. In these pulsed induction linear accelerator systems, electrical energy is stored in a component such as a capacitor or pulse forming line or network. Then a switch is utilized to discharge the voltage across a vacuum gap. Charge particles in the vacuum gap will then undergo acceleration. In a linear system, because of the difficulty associated with attempting to accelerate charge particles to high energy across a single acceleration gap, multiple gaps are used. But in so doing, a means of isolating each gap is required. One method for this isolation can be done either by using a magnetic core in the acceleration gap or by transit time isolation Further, although linear is a preferable configuration for the accelerator, devices using magnetics can also be circular or spiral to save space. For instance, a dipole magnet or sector dipole magnets, can be used to bend the particle in such an orbit to thread either single or multiple induction cavities driven by high voltage pulsers. As the particles gain energy, the magnetic field can be increased to maintain the same orbit so as to continue to transit through the induction cavities. Once the particles reach the required energy, they can be deflected from the system. This technique is starkly different from devices such as synchrotrons in that the intermediate and potentially wasteful step of creating RF or microwave energy to drive a resonant cavity is no longer needed. However, the disadvantage of circular systems, at least for electrons, is that energy losses can be high.

As known by those skilled in the art, the radiation dose rate created, for instance, by electrons impinging on a bremsstrahlung conversion target is approximately proportional to the incident beam current multiplied by the energy of the electrons to the 2.7 power. The total dose is then equal to the pulse width times the dose rate. Thus, control of dose rate and dose can be realized by controlling any or a combination of beam current, electron energy, or pulse temporal shape. Since research has shown that dose rate is critical in this application, a means is necessary to control the dose rate in real time during the treatment and total dose at the end is necessary to meet the requirements prescribed by the treating clinicians.

One example of a pulsed type accelerator system is described in U.S. Pat. No. 7,710,051 to Caporaso, et. al. Among other differences, in that configuration, beam intensity and beam energy were controlled but beam current was not controlled and dose rate was not anticipated or addressed as a controllable parameter.

Beam energy will determine penetration depth and so to control dose rate for a given penetration depth requires maintaining constant energy while controlling the current either injected into the accelerator by the particle generator or within the accelerator itself. To control total dose for the specified dose-rate, the temporal character of the individual pulse or pulses which accelerate the charged particle would then need to be controlled. Conversely, if time shape of the applied pulse were the controlling parameter used to control dose in a pulsed machine driven by high voltage pulse sources, beam current could be increased or decreased as necessary for the given treatment time. All these approaches require control of an active switch.

The active switch utilized to discharge voltage across a vacuum gap is an enabling component of an accelerator system in accordance with the disclosed embodiments. It must reliably hold off high voltage until the voltage is required across the acceleration gap, turn on precisely when required, allow a controlled flow of current (typically 10's to many 100's of amps) for the desired time and turn off within 10's of nanoseconds from command to turn off consistently when required. This sequence must be performed repeatedly at a required rate for a specified number of times in order for the total required dose to be delivered. In addition, the switch needs to be able to be infinitely variable in the on-state conditions so as to precisely control the dose rate output of the accelerator. Desired characteristics of the switching device include for pulses, variable pulse time length; turn on and turn off times much shorter than the pulse time; switching control unaffected by the high voltage action; long lifetime and simplicity of use. While such a capability may be achievable at low voltages with transistors and MOSFETS, demands for accomplishing this demanding application at voltages necessary for a pulsed power accelerator (approximately 10's to 100's of kilovolts) are extremely unique. Because of this unique requirement, such a switch has not been implemented in a pulsed power accelerator, and existing systems that use inductive coupling or discharge gas switches do not fulfill all the switching requirements, are overly complex and are thus undesirable.

One switching configuration that can be used with an ultra-high dose rate therapy system in some applications uses an inductive voltage adder. While the basic configuration that includes transistors and MOSFETS by themselves are incapable of switching at these levels, a combination of series and parallel arrangements are able to. The difficulty with this arrangement though is how to drive the control terminals of these devices from a ground potential source. One solution is to simplify this problem by using inductive coupling of a combination of series and parallel transistors at ground potential.

According to an embodiment of the disclosed technology, the switch device is a photoconductive switch. Such a switch is an electrical device that operates based on the optical conductivity of a material in response to light. That is, the electrical conductance of the switch is increased as a consequence of irradiation with light. Photoconductive devices are more capable of handling high voltages than junction devices due in part to bulk conduction, which is the process where close to the entirety of the device is turned on simultaneously. In a preferred embodiment of the disclosed technology, a photoconductive charge trapping apparatus is used as the active switching device because of its high voltage and high pulsed current capability in a compact package. For example, a photoconductive switch device can be used that utilizes a light source configured to emit light that is received by a crystalline material (e.g., comprising silicon carbide) of the photoconductive switch. The crystalline material is doped with a dopant (e.g., vanadium, nitrogen, aluminum, or boron) that forms a mid-gap state within a bandgap of the crystalline material to control a recombination time of the crystalline material, and the crystalline material is configured to exhibit a substantially linear transconductance in response to receiving the light from the light source. The switch also includes a first electrode coupled to the crystalline material to provide a first electrical contact for the crystalline material, and a second electrode coupled to the crystalline material to provide a second electrical contact for the crystalline material. The first and the second electrodes are configured to establish an electric field across the crystalline material. It should be noted, however, that other types of switches that satisfy the above noted criteria can also be used.

Because the photoconductive active switching devices are very agile, adjusting the beam current, final energy, or temporal behavior can be implemented to produce the desired characteristics. Current produced by the radiation source can be controlled by a grid system in the source of charged particles, e.g., an injector or particle generator. As an alternative, by changing the potentials within the injector, beam current can also be controlled. Further, to control the particle energy, the voltage at the vacuum gap can likewise be controlled. By controlling the temporal character of the applied voltages to either the grid or vacuum gap, the dose rate can then be controlled.

FIG. 1 illustrates a block diagram of a particle accelerator system for radiotherapy applications in accordance with an example embodiment. As shown in FIG. 1, the system includes an energy source 102, a voltage shaping switch 104 and a particle accelerator 106. The energy source can be, for example, one or more capacitors or another source that is capable of supplying high voltage values in the range of 10-100's of kilovolts. The system in FIG. 1 allows control of accelerator energy, current and/or dose rate using the voltage shaping switch 104 by, for example, actively controlling the conductance of the switch and/or on-off times of the switch. The switch 104 can be a photoconductive switch, as described earlier, configured to produce the desired shape (e.g., top hat pulses with suitable duty cycle, width and amplitude).

Figure 2:
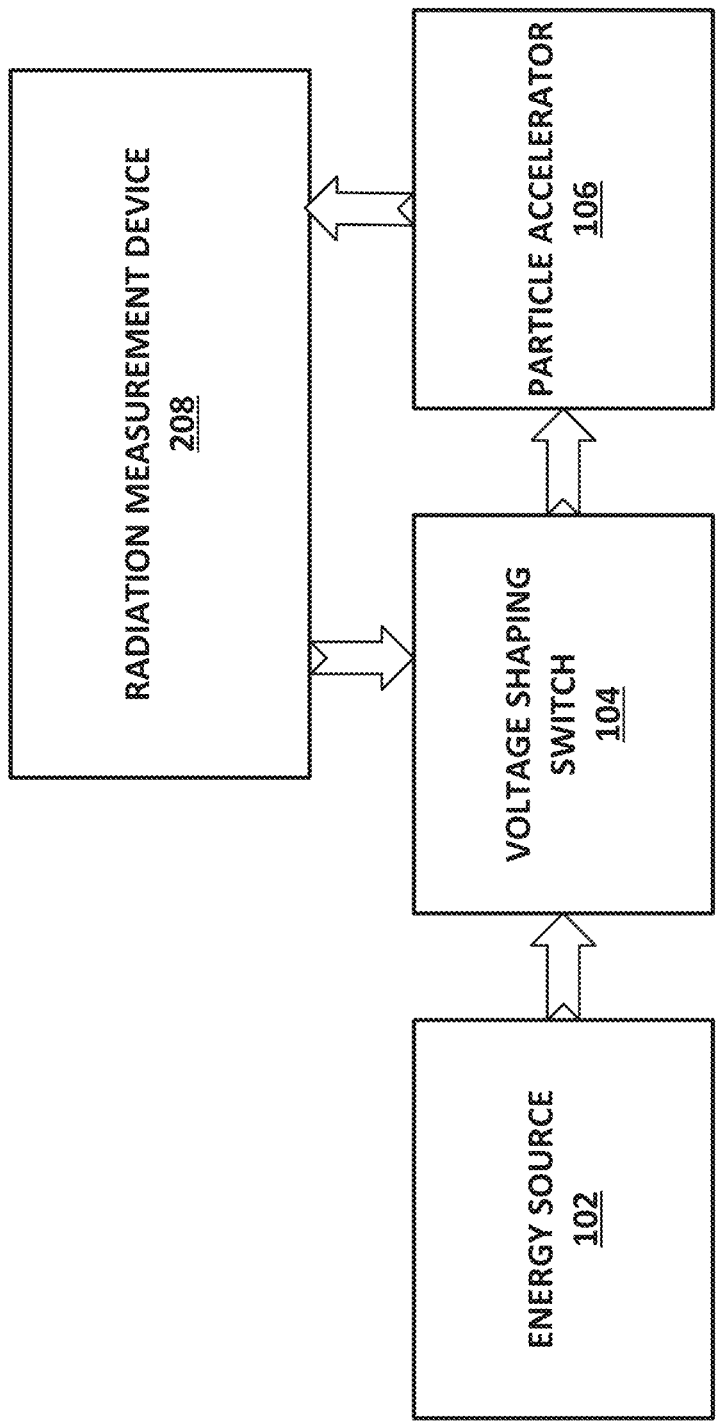
FIG. 2 illustrates a block diagram of a particle accelerator system for radiotherapy applications that includes a radiation measurement device in accordance with an example embodiment.

FIG. 2 illustrates another block diagram of a particle accelerator system that additionally includes a radiation measurement device 208 that is configured to measure the output radiation and to provide feedback to the voltage shaping switch 104. For example, dose and dose rate can be measured by placing a material that is relatively transparent to the beam between the accelerator and patient. When the radiation interacts with the material, charge carriers are created through various physical processes that can be monitored by an external circuit. For this particular application, where high dose rates ($10^5$ Gy/s) and fast pulses (10's of nanoseconds) need to be adequately monitored, both damage of the detector and speed are very important. In such a case, diamond based detectors with stripline electrodes for response speed may be necessary. The voltage shaping switch can adjust the shape of the voltage waveform that is supplied to the accelerator based on the measured radiation. For example, the temporal pulse shape of the voltage waveform can be changed to adjust the administered dose. For instance, pulse amplitude, repetition rate and the pulse shape can all be adjusted.

For illustrative purposes, in more complex particle accelerator systems, such as for instance a betatron, the rate at which the electrons gain energy is proportional to the time rate of change of an increasing magnetic field. The magnetic field, under the proper conditions, also confines the electrons to a circular orbit while accelerating them. The final energy of the electrons in such a system is proportional to the peak magnetic field achieved during the acceleration process. In existing systems, thyratrons are typically used to control the increasing magnetic field. However, typical thyratrons have very little controllability once they are triggered into a conducting state. Thus, more complex means are required to control the dose rate produced by such an arrangement. High power switches can provide a controllability of the magnetic field rate of increase and peak final energy and therefore readily control dose rate.

Figure 3:
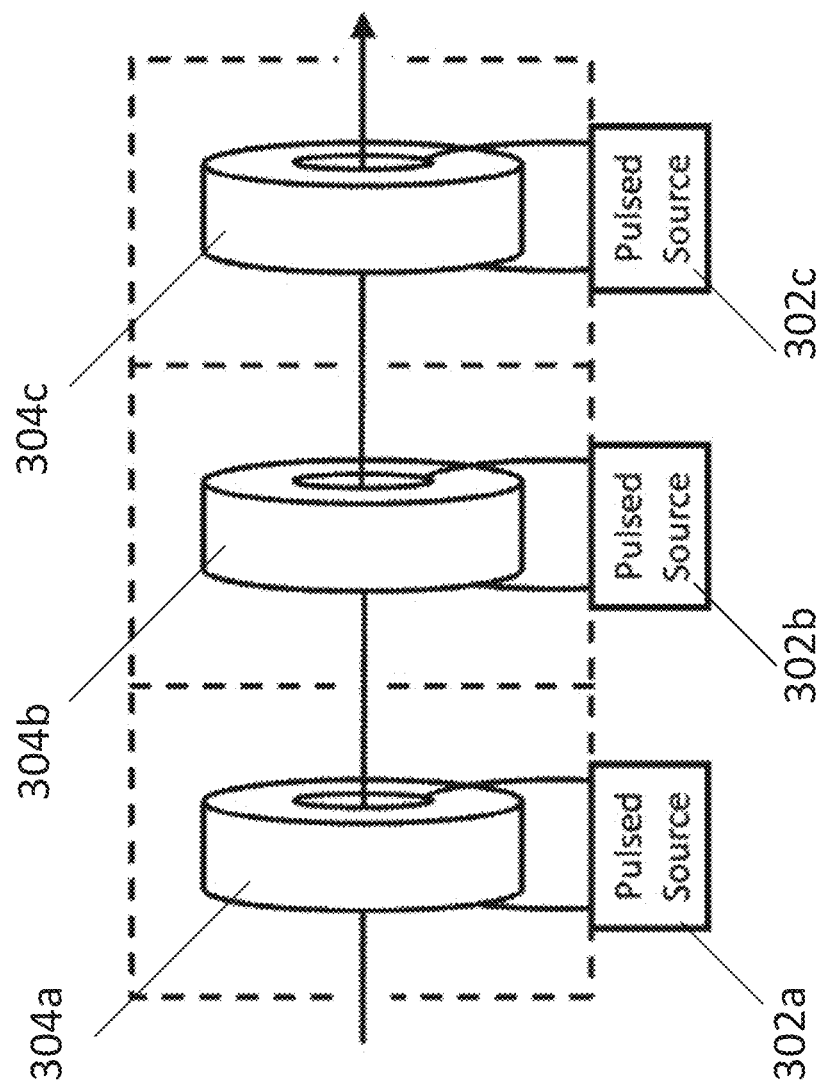
FIG. 3 illustrates the basic components of an induction linear accelerator.

More direct control is afforded by controlling the potential applied to a series of vacuum gaps used in an accelerator. This approach is particularly suited for a particular type of system called an induction linear accelerator. The operation of the accelerator is straightforward and is widely documented. The overall system can be thought of, in simple terms, as a series of 1:1 magnetic core transformers, where pulsed voltage sources form the transformer primary circuit and the charged particle beam pulse acts as the secondary. FIG. 3 illustrates a schematic of an induction linear accelerator, in which pulses sources 302a, 302b, 302c are applied to three corresponding magnetic cores 304a, 304b, 304c, and the path of the charged particle beam is illustrated by the arrow through the center of the cores.

Figure 4:
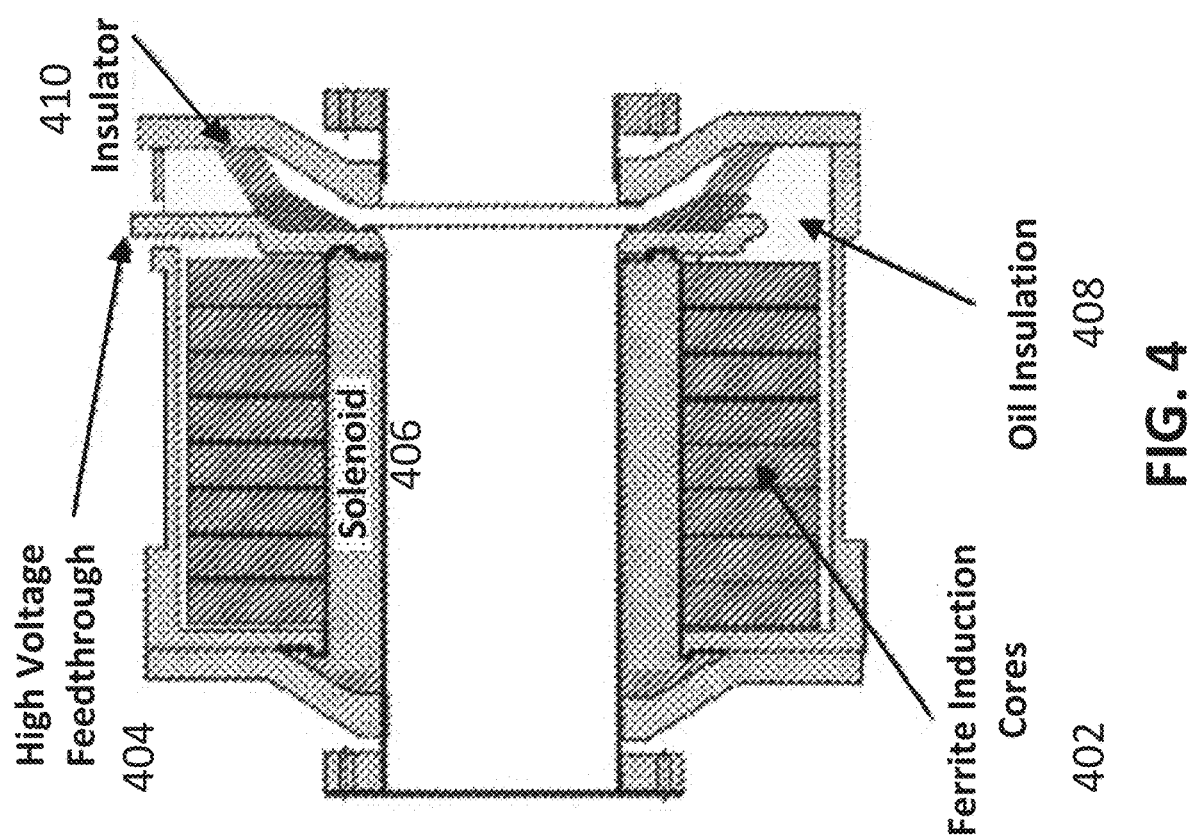
FIG. 4 illustrates components of an induction linear accelerator.
Figure 5:
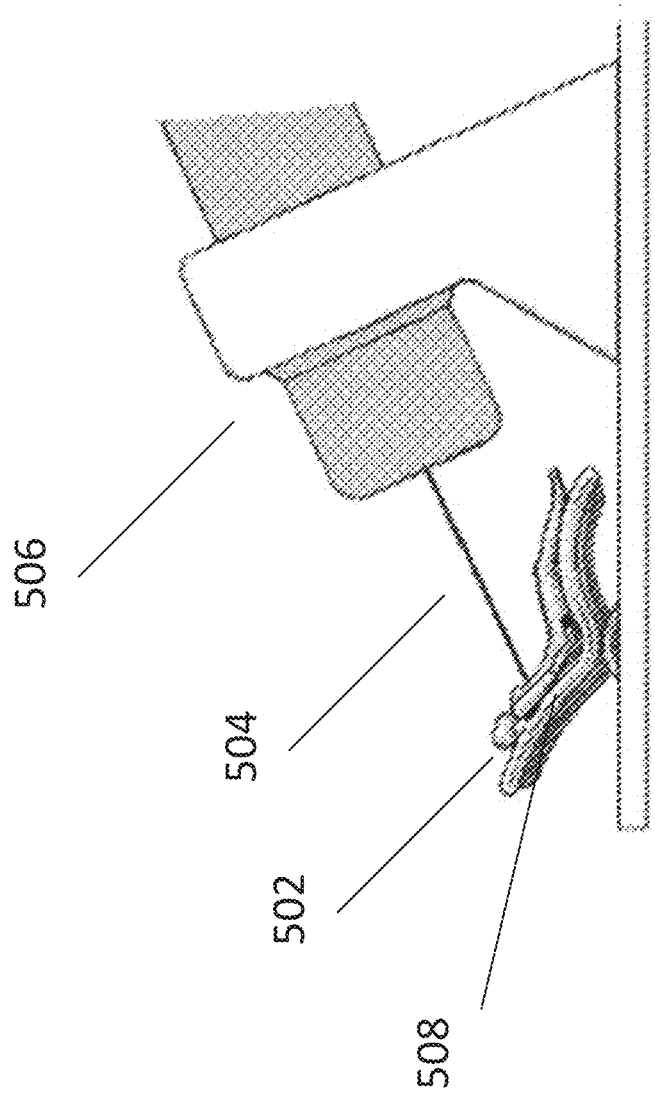
FIG. 5 is an illustration of a single axis radiotherapy system that can be used to administer FLASH radiotherapy.

FIG. 4 illustrates an example accelerator cell implemented in the Experimental Test Accelerator-II (ETA-II). The cell includes ferrite induction coils 402, high voltage feedthrough 404, solenoid 406, oil insulation 408 and insulator 410. When a pulsed voltage is applied to the high voltage feedthrough 404, the magnetic induction created by the current flowing on the internal wall creates an accelerating potential across the insulator 410. Electrons in the gap next to the insulator are therefore accelerated so long as the potential is maintained during the pulse. The solenoid 406 keeps the electrons focused along the accelerator. In a typical implementation of the system, each magnetic core forms an electrically isolated accelerator cell. This approach provides electrical isolation between each of the magnetic core-pulsed source combination units with only the beam action being common. This isolation allows each unit to function essentially independently of the other sources. The configuration that is shown in FIG. 4 is capable of producing approximately 6 MeV electrons at 2 kA in 70 ns pulses at a 5 kHz repetition rate. Converted to x-rays, these parameters indicate an instantaneous dose rate of approximately 4-MGy/s at 0.275-Gy/pulse or approximately 1.4 kGy in a 1-s burst. Thus, dose rate and total dose would be significant from such machines. An example of such a radiotherapy system using the above noted accelerator is depicted in FIG. 5, illustrating a patient 502 that receives radiation 504 from a single axis radiotherapy system 506.

Because of the ultra-high dose rates and the short amount of time involved in this therapy method, it is critically important that the patient be adequately supported and stationary when the radiation dose is administered. Such a method is shown schematically in FIG. 5, where the couch/bench 508 can employ conformal supports that are made by 3D scanning of the patient and using that information to make a custom fitting support. Or by the use of inflatable bladders to ensure that the patient is immobilized sufficiently during the set-up, aiming, and treatment of the patient.

The pulsed source for such a system may utilize configurations that charge energy storage components such as capacitors in parallel but discharge them into the accelerator cell in series. In this way, only a lower, more manageable voltage is used to the exterior of the accelerator pulser with the high voltage being confined mainly to the accelerator cell itself.

Finally, managing the electric fields in the vacuum gap can be quite challenging at times. However, under pulsed conditions, various coatings can be used to prevent the precursor to electrical breakdown. For instance, "greening" (firing an electropolished stainless steel surface in wet hydrogen for one hour at 950° C.) increases the threshold of pre-breakdown electrical phenomena by a factor of more than two. To manage breakdown at the vacuum interface, use of a multilayer insulator would enable higher gradients than could normally be obtained. This type of insulator also enables the use of a straight wall configuration that is much easier to implement. Tests have also shown that this type of insulator is robust even in high radiation environments and that certain beam instabilities can be suppressed.

Another aspect of radiation treatment is providing multiple lines of site to achieve better conformity to the target tumor. Induction linear accelerators easily allow for this possibility. Such systems have been proposed for tomographic flash x-ray radiography systems. In one approach, a single accelerator generates an intense short pulse electron beam that is directed into multiple beamlines by a system of kickers and electromagnets. A beam optics system then directs the beams to a central point to enable 3D reconstruction of the object of interest. The system was intended to be multi-pulse to produce multi-frame images at multiple lines of sight to enable tomographic reconstruction of a dynamic test. Such a system approach is similarly possible for use as a FLASH radiotherapy source.

Because the gradient in an induction linear accelerator is not dependent on the diameter of the beam pipe diameter, it can be made arbitrarily large. This unique feature enables the acceleration of multiple beams through the same accelerator. Thus, by creating multiple beamlets at the entrance of the accelerator, these beamlets can be transmitted separately in parallel to "catcher" optics to extract the beamlets and keep them separate. As separate beamlets, they can then be directed to the patient from multiple angles with various bending optics.

The iris loaded RF linear accelerator used in conventional radiotherapy, while it could possibly be configured for such an arrangement, is less practical. Since this type of accelerator needs to be treated as a waveguide structure, the inner iris radius, where the beam is being accelerated, would need to be enlarged. This enlargement lowers the impedance of the structure and requires increased RF power for a given gradient. The advantage of the previously described induction linear accelerator is that the acceleration gradient is largely independent of the inner radius. So, enlargement of the beam pipe to accommodate multiple beams will have little effect on the power requirements. Such an approach of propagation of multiple beams in induction accelerators has been studied for use in heavy ion fusion systems, and can be similarly implemented in the disclosed FLASH radiotherapy systems as noted above.

As explained earlier, FLASH radiotherapy is administered with a sequence of short micro-pulses over a short period of time. The most recent literature requires that for healthy tissue to be spared during irradiation, five conditions or requirements must be fulfilled.

The first is that the instantaneous dose rate (dose within a micro pulse) exceed $1.8 \times 10^5$ Gy/s. The second is that the irradiation time to administer the required dose must be less than 200 ms. Third, as the full radiation dose is typically 8-20 Gy, the average dose rate during the 200 ms period must be between 40-100 Gy/s. Fourth, the entirety of the irradiated region must be above both the instantaneous and average dose rates. As such narrow beams with Gaussian or similar intensity profiles cannot fulfill this requirement without damaging the surrounding healthy cells. And finally, for the system to be useful for therapy in a clinic setting, the system needs to be less than 100 $m^3$. And of course, because the radiation during this short period must be monitored and controlled very precisely for the patient's long-term health, a means which can both monitor and control the administered dose on these very short, intense, and demanding time scales must be implemented. Meeting all these requirements simultaneously is clearly quite demanding and has not been met to date despite numerous research and development efforts and large sums of money invested to develop such products.

Several less than complete approaches by those highly skilled in the art of radiation therapy have been proposed and studied. Some of these were described earlier in this patent document. But unfortunately, all of the attempts, while potentially meeting some, do not meet all of the aforementioned demanding requirements.

For instance, many have proposed and studied the use of hadron particles, in particular protons and certain heavy particles from cyclotrons, synchrotrons, and similar type machines. Unfortunately, for hadrons to be useful, they must have substantial energy to penetrate the human torso where a tumor can reside. In such a case, for protons, the energy must be about 200 MeV. Such a machine and the ancillary equipment would have cannot be practically confined to a 100 $m^3$ volume.

But more importantly, the beam emanating from such a device comes out in the form of a pencil beam of approximately 1 cm diameter with the edges approximating a Gaussian shape. Hard-edge beams are technologically extremely difficult to achieve. So, while the beam center may meet the above healthy tissue sparing requirements, the edges do not. The net result is while the irradiation at the beam core may be at the healthy tissue sparing threshold, that at the beam edges is not and would result in healthy tissue damage. While raster scanning may expand the irradiation volume, the same issue of damaging healthy tissue in the beam edges remains.

Still another approach under consideration by those highly skilled in the art of radiation therapy is to use a microwave linear accelerator to create an electron beam. The most significant difficulty with such devices is the limitation on the peak current that can be achieved. Two fundamental issues make achieving high instantaneous dose rate extremely difficult to achieve technologically. First, high currents require high power, placing extreme demands on the overall system. Secondly, high current creates a natural beam instability that shortens the pulse and thus prevents delivery of the required dose rate. This latter problem is so fundamental, that highly skilled innovators in the art have resorted to designing a system requiring sixteen distinctly separate accelerators placed symmetrically about the patient with the beams converging on the irradiation volume. Such a system is expensive, bulky and impractical to implement.

Yet another approach under consideration by those highly skilled in the art of radiation therapy is to use a conventional single accelerator or an x-ray tube in very close proximity to the desired irradiated volume. Such an approach may be able to meet the above requirements in a small volume very local to the exit of the accelerator. Unfortunately, with the exception of hadron particles, radiation attenuates exponentially as it enters matter. The net result is that while the above requirements may be met at or near the surface, deeper into the tissue, the healthy tissue sparing effects are not met and again those tissues are damaged.

Pulsed power is the field of expertise whereby energy is stored in a storage element and is suddenly discharged by some type of switching means, delivering a pulse into a load. Typical levels are 1000s of amperes at 10,000s of volts in 10s of billionths of a second; that is, peak powers of 10s of megawatts. Because the currents involved are quite large, the switching means required is bistable. That is the switch stays non-conducting until some type of event trigger occurs. After that event trigger occurs, the switching element stays conducting until charge carriers have sufficient time to quench so that a restrike (e.g., an uncontrolled closing) does not occur. Amplitude of the pulse and the pulse width are largely uncontrollable so that the output pulse is not determinable by the switch; significant variation can occur pulse to pulse. Thus, such systems are highly non-linear, relying on avalanche phenomena, and therefore lack precise control (~5%), making them unsuitable for FLASH radiotherapy. While pulsed power is consistent with the instantaneous dose rate requirements of FLASH radiotherapy, the overall techniques are inadequate for high average dose rates.

FLASH treatment also requires that these pulses be stably produced in a repeatable fashion and controlled at a high repetition rate typically exceeding 1 kHz and more preferably 10 kHz and beyond. Typical pulsed power systems are generally incapable of such repetition rates.

Some attempts in the state-of-the-art pulsed power systems have focused on moderate repetition rates that would limit the average dose rate requirements for FLASH, yet these means are largely uncontrollable. While MOSFET switching approaches are controllable and have the potential for implementation in radiotherapy, a full system would be highly cumbersome and not meet the 100 m$^3$ requirement. For instance, a system that is capable of penetrating the human torso with electrons that were converted to Bremsstrahlung would require over one hundred thousand transistors and the ancillary circuit elements. And even photoconductive switches, if used in a non-linear mode as is typically done, are incapable of rapid repetition rates as would be required for this purpose.

The FLASH radiotherapy systems disclosed herein are capable of meeting all five aforementioned requirements at least in-part by actively controlling the operation of the photoconductive switch that is operable in a substantially linear transconductance region. In particular, the disclosed systems can achieve instantaneous dose rates that exceed $1.8 \times 10^5$ Gy/s, can administer the required dose in less than 200 ms, with average dose rates between 40-100 Gy/s, and can provide the entirety of the irradiated region with levels above both the instantaneous and average dose rates. Furthermore, the system can be implemented in a compact form that occupies less than 100 m$^3$. The disclosed FLASH radiotherapy systems that would meet all the aforementioned requirements can include a power supply for charging an energy storage, connected to a controllable switching means, connected to a means of creating radiation for FLASH radiation, whereby the radiation is created by the high voltage pulse applied to a set of electrodes. The system can also include a means of measuring the radiation administered to the patient, whereby the switching means controls the dose by the pulse amplitude, the pulse width, or the number of pulses being administered. The combination of these complex key elements produces a compact system that meets all of the five aforementioned requirements, and is operable to flexibly meet the requisite dose rates and other operational conditions. For example, the described photoconductive switches have very high breakdown voltages. For instance, a piece of silicon carbide, used in the proper configuration, is capable of withstanding 20 kV over 0.3 mm. The disclosed photoconductive switches are further characterized by short response times, typically on the 1-10 ns times or less, thus allowing the output pulses to be appropriately modulated and shaped to meet the above noted requirements. Furthermore, the switch has a relatively small footprint, typically less than 10 cm$^3$ that enable the system to be implemented within a 100 cubic meter facility.

Figure 6:
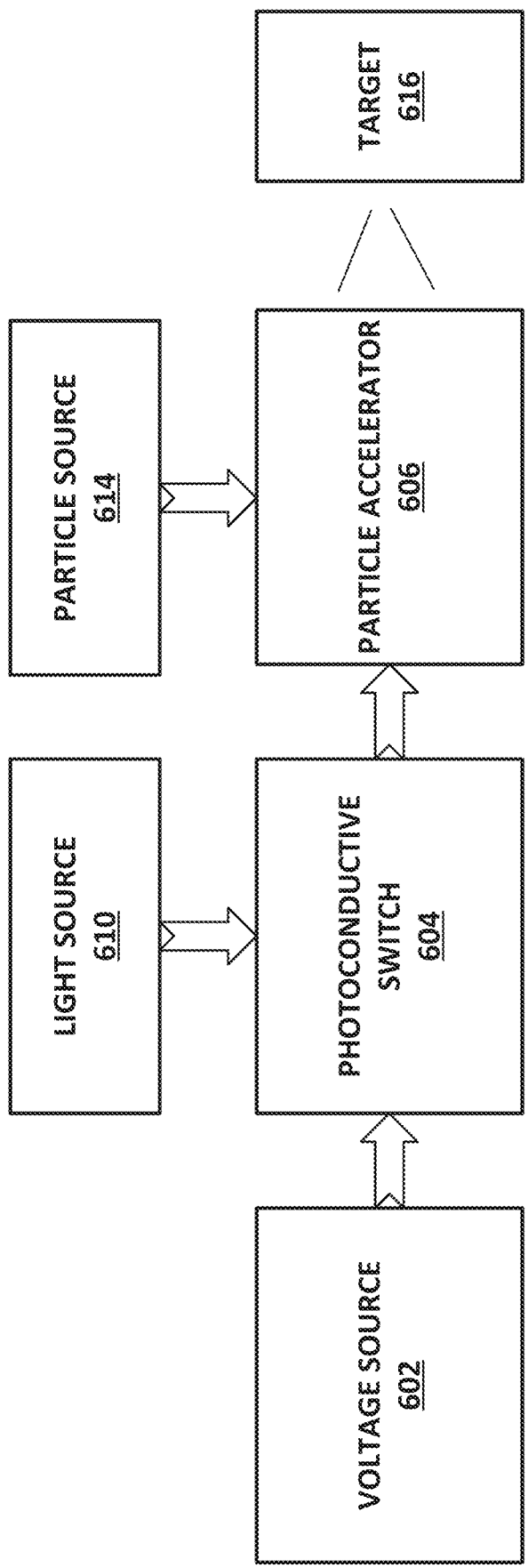
FIG. 6 illustrates a block diagram of FLASH radiotherapy system that includes a particle accelerator system in accordance with an example embodiment.

FIG. 6 illustrates an example FLASH radiotherapy system in accordance with an example embodiment. The system includes a photoconductive switch 604 that is coupled to a voltage source 602 (e.g., a high-voltage source capable of producing voltage values in the range 10-100 kV. The voltage source 602 can be coupled to a first and a second electrode of the photoconductive switch to establish an electric field across the switch 604. In an embodiment, the photoconductive switch 604 includes a crystalline material that exhibits a substantially linear transconductance in response to receiving light from the light source 610. The light source can include one or more lasers that are operable to excite the charge carriers in the crystalline material and to cause the switch to operate. A particle source 614 supplies particles (e.g., electrons or any charged particle useful for ultra-high dose rate therapy) to the particle accelerator 606. The photoconductive switch 604 is coupled to the particle accelerator 606 and supplies the appropriate number of pulses of particular shape, amplitude, duration and duty cycle to accelerate the charged particles. By controlling the pulses supplied to the particle accelerator 606, a specific dose rate, average dose and/or beam energy can be delivered to the target 616 (e.g., patient). Similar to FIG. 2, a radiation measurement device can also be incorporated into the system of FIG. 5, where the measured radiation can be used as a control feedback to modify the activation of the photoconductive switch 604 and to modify the voltage pulses that are output from the photoconductive switch 604.

It should be noted that in example embodiments of the radiotherapy systems, a pulsed source feeds the accelerator directly without using an intermediate RF producing system to feed the accelerator.

One example FLASH radiotherapy accelerator system according to the disclosed embodiments includes of a charge particle accelerator used to accelerate charged particles, and an actively controlled switching means to affect the dose rate by affecting the beam current, the beam energy, or the temporal shape of the applied pulse used to impart energy to the charged particles. The charged particle accelerator can be a charged particle accelerator delivering one or more separate pulses.

In another example, a FLASH radiotherapy accelerator system includes a support structure, an accelerator, a charged particle generator connected to the accelerator for producing and injecting a charged particle beam into the accelerator. The FLASH radiotherapy accelerator system also includes an actively controlled switching means connectable to a high voltage potential for propagating at least one electrical wavefront to impress a pulsed gradient which imparts energy to the injected beam, where the switching means controls the dose rate by affecting the beam current, the beam energy, or the temporal shape of the applied pulse.

In yet another example, a FLASH radiotherapy accelerator system includes a support structure, an accelerator, and a charged particle generator connected to the accelerator for producing and injecting a charged particle beam into the accelerator. The FLASH radiotherapy accelerator system also includes an actively controlled switching means connectable to a high voltage potential for propagating at least one electrical wavefront to impress a pulsed gradient which imparts energy to the injected beam, where the switching means controls the dose rate by affecting the beam current, the beam energy, or the temporal shape of the applied pulse. The switching means can be a photoconductive device that includes a light source configured to emit light, a crystalline material positioned to receive the light from the light source, wherein the crystalline material is doped with a dopant that forms a mid-gap state within a bandgap of the crystalline material to control a recombination time of the crystalline material. The photoconductive device also includes a first electrode coupled to the crystalline material to provide a first electrical contact for the crystalline material, and a second electrode coupled to the crystalline material to provide a second electrical contact for the crystalline material, wherein the first and the second electrodes are configured to establish an electric field across the crystalline material, and wherein the crystalline material is configured to exhibit a substantially linear transconductance in response to receiving the light from the light source.

In yet another example, a FLASH radiotherapy accelerator system includes a support structure, an induction accelerator, a charged particle generator connected to the accelerator for producing and injecting a charged particle beam into the accelerator, an actively controlled switching means connectable to a high voltage potential for propagating at least one electrical wavefront to impress a pulsed gradient which imparts energy to the injected beam. The switching means controls the dose rate by affecting the beam current, the beam energy, and/or the temporal shape of the applied pulse. The switching means can be a photoconductive device, that includes a light source configured to emit light, a crystalline material positioned to receive the light from the light source, wherein the crystalline material is doped with a dopant that forms a mid-gap state within a bandgap of the crystalline material to control a recombination time of the crystalline material. The switching means also includes a first electrode coupled to the crystalline material to provide a first electrical contact for the crystalline material, and a second electrode coupled to the crystalline material to provide a second electrical contact for the crystalline material, wherein the first and the second electrodes are configured to establish an electric field across the crystalline material, and wherein the crystalline material is configured to exhibit a substantially linear transconductance in response to receiving the light from the light source.

Another example FLASH radiotherapy accelerator system includes a charge particle accelerator used to accelerate charged particles delivered in a pulse, an actively controlled switching means to affect the dose rate by affecting the beam current, the beam energy, or the temporal shape of the applied pulse used to impart energy to the charged particles, where the actively controlled switching means is controlled by a controller. For example, the controller can actively control the switching means based on the measurement of the radiation from the charge particles. In some implementations, a beam transport system is used to capture and transport multiple separate beams to enable treatment using more than one line of sight.

Figure 7:
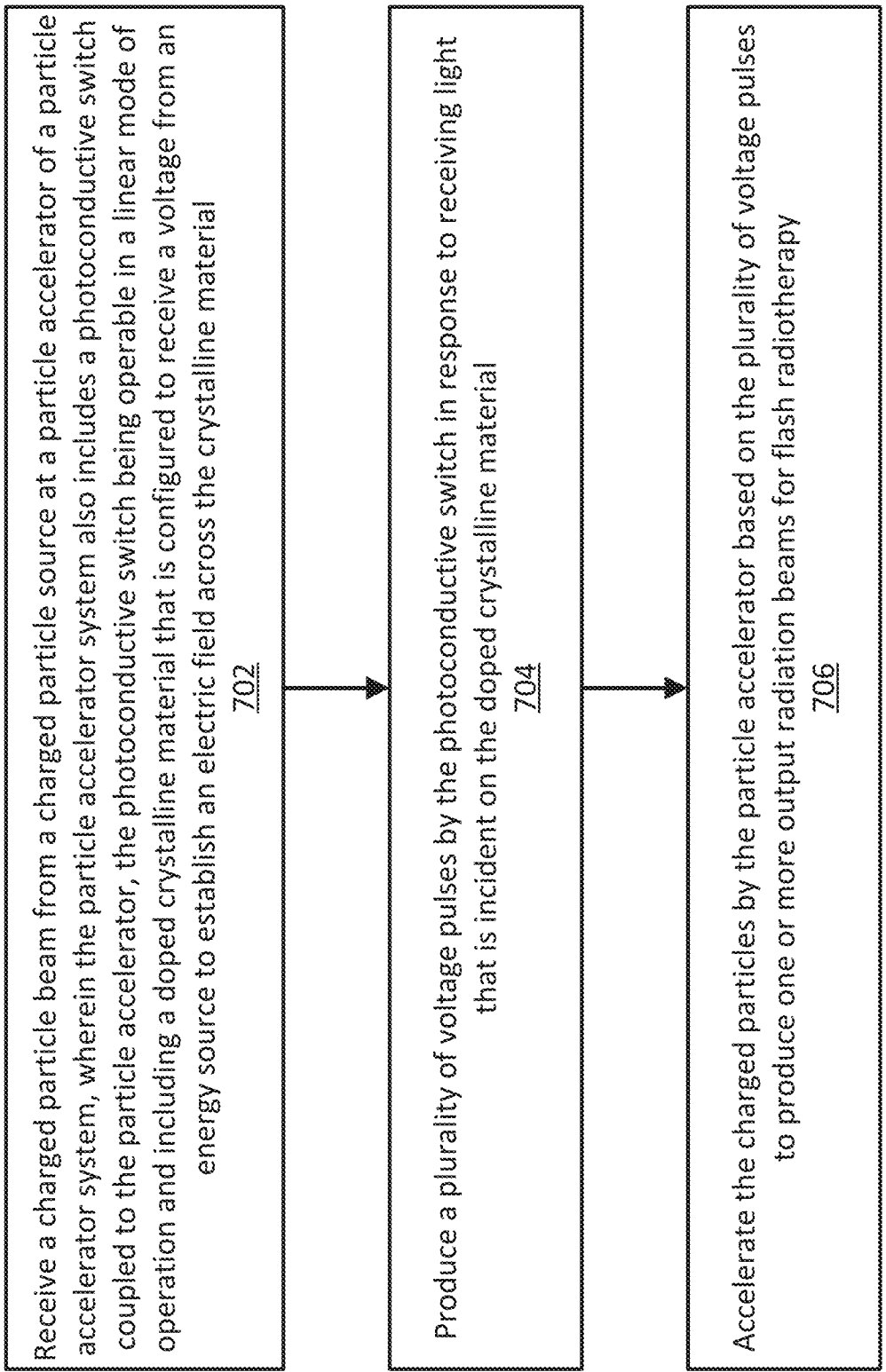
FIG. 7 illustrates a set of example operations that can be carried out to produce an output radiation beam in a FLASH radiotherapy system in accordance with an example embodiment.

FIG. 7 illustrates a set of example operations that can be carried out to produce an output radiation beam in a FLASH radiotherapy system in accordance with an example embodiment. At 702, a charged particle beam from a charged particle source is received at a particle accelerator of a particle accelerator system. The particle accelerator system also includes a photoconductive switch coupled to the particle accelerator, the photoconductive switch being operable in a linear mode of operation and including a doped crystalline material that is configured to receive a voltage from an energy source to establish an electric field across the crystalline material. At 704, a plurality of voltage pulses is produced by the photoconductive switch in response to receiving light that is incident on the doped crystalline material. At 706, the charged particles are accelerated by the particle accelerator based on the plurality of voltage pulses to produce one or more output radiation beams for FLASH radiotherapy.

In one example embodiment, the above noted operations further include measuring the one or more output radiation beams, and modifying one or more of an amplitude, shape, spacing, number or width of the plurality of voltage pulses supplied to the particle accelerator based on measurement of the one or more output radiation beams. In another example embodiment, the disclosed operations include producing the one or more output radiation beams that include radiation pulses with an instantaneous dose rate that exceed $1.8 \times 10^5$ Gy/s, administering a required dose in less than 200 ms, producing the one or more output radiation beams having radiation pulses with an average dose rate between 40-100 Gy/s, and irradiating an entirety of a target region with levels above both the instantaneous and the average dose rates.

According to another example embodiment, the above noted operations include modifying an energy, instantaneous dose rate or average dose rate of the one or more output radiation beams based on the plurality of voltage pulses produced by the photoconductive switch. In one example embodiment, at least one of the plurality of voltage pulses has a non-Gaussian profile. In another example embodiment, at least one of the plurality of voltage pulses has a top hat profile.

Another aspect of the disclosed embodiments relates to an accelerator system for use in a flash radiotherapy system that includes a particle accelerator configured to receive charged particles, and a photoconductive switch coupled to the particle accelerator and configured to supply the particle accelerator with a plurality of voltage pulses, wherein the particle accelerator is operable to accelerate the charged particles based on the plurality of voltage pulses, and to produce an output beam comprising one or more radiation pulses for flash radiotherapy. The photoconductive switch is configured to receive light from a light source and to operate in response to the received light; the photoconductive switch is operable in a linear mode of operation in response to the received light. The photoconductive switch also includes a doped crystalline material that is configured to receive a voltage from an energy source to establish an electric field across the crystalline material, and is operable to modify one or more of an amplitude, shape, spacing, number or width of the plurality of voltage pulses supplied to the particle accelerator.

In one example embodiment, the photoconductive switch is operable to modify an energy, instantaneous dose rate or average dose rate of the output radiation pulses based on modification of the one or more of amplitude, shape, spacing, number or width of the plurality of voltage pulses supplied to the particle accelerator. In another example embodiment, the photoconductive switch is configured to receive feedback information associated with a measurement of the one or more output radiation pulses, and is operable to modify the one or more of amplitude, shape, spacing, number or width of the plurality of voltage pulses based on the feedback information. In yet another example embodiment, the accelerator system includes a radiation measurement device configured to conduct the measurement of the one or more output radiation pulses.

According to another example embodiment, the accelerator system has a three-dimensional footprint of less than or equal to 100 cubic meters. In still another example embodiment, the accelerator system is operable to: produce the output radiation pulses with an instantaneous dose rate that exceed $1.8 \times 10^5$ Gy/s, administer a totality of the output radiation pulses that constitute a required dose in less than 200 ms, produce the output radiation pulses with an average dose rate between 40-100 Gy/s, and irradiate an entirety of a target region with levels above both the instantaneous and average dose rates. In one example embodiment, one or more of the plurality of voltage pulses has a non-Gaussian profile. In another example embodiment, the one or more of the plurality of voltage pulses has a top hat profile.

In one example embodiment, the particle accelerator is an induction linear accelerator. In another example embodiment, the accelerator system includes the light source, wherein the light source includes one or more laser sources. According to yet another example embodiment, the accelerator system includes the energy source that is coupled to the photoconductive switch. In one example embodiment, the energy source comprises one or more capacitors. In another example embodiment, the energy source comprises a voltage source that is coupled to a first and a second electrode of the photoconductive switch. In still another example embodiment, the charged particles comprise electrons. In yet another example embodiment, the particle accelerator includes a beam pipe that accommodates multiple charged particle beams therein.

Another aspect of the disclosed embodiments relates to a flash radiotherapy system that includes an induction accelerator, a controllable switch coupled to the induction accelerator and operable to produce a plurality of voltage pulses to drive the induction accelerator, and a radiation measurement device configured to measure output radiation produced by the flash radiotherapy system and provide feedback to the controllable switch. The controllable switch is operable to modify the plurality of voltage pulses based on the feedback from the radiation measurement device. In one example embodiment, the flash radiotherapy system also includes a patient immobilization means for situating a patient in a stationary position at a particular position in a path of the output radiation. Such a system can produce an average dose rate of greater than 40 Gy/s.

While this document contains many specifics, these should not be construed as limitations on the scope of an invention that is claimed or of what may be claimed, but rather as descriptions of features specific to particular embodiments. Certain features that are described in this document in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

It is understood that at least some of the component of the disclosed embodiments may be implemented individually, or collectively, in devices comprised of a processor, a memory unit, an interface that are communicatively connected to each other. The processor and/or controller can perform various disclosed operations based on execution of program code that is stored on a storage medium. The processor and/or controller can, for example, be in communication with at least one memory and with at least one communication unit that enables the exchange of data and information, directly or indirectly, through the communication link with other entities, devices and networks. The communication unit may provide wired and/or wireless communication capabilities in accordance with one or more communication protocols, and therefore it may comprise the proper transmitter/receiver antennas, circuitry and ports, as well as the encoding/decoding capabilities that may be necessary for proper transmission and/or reception of data and other information.

Various information and data processing operations described herein may be implemented in one embodiment by a computer program product, embodied in a computer-readable medium, including computer-executable instructions, such as program code, executed by computers in networked environments. A computer-readable medium may include removable and non-removable storage devices including, but not limited to, Read Only Memory (ROM), Random Access Memory (RAM), compact discs (CDs), digital versatile discs (DVD), etc. Therefore, the computer-readable media that is described in the present application comprises non-transitory storage media. Generally, program modules may include routines, programs, objects, components, data structures, etc. that perform particular tasks or implement particular abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps or processes.

Only a few implementations and examples are described, and other implementations, enhancements, and variations can be made based on what is described and illustrated in this disclosure.

What is claimed is:

1. An accelerator system for use in a flash radiotherapy system, comprising:
   a particle accelerator configured to receive charged particles; and
   a photoconductive switch coupled to the particle accelerator and configured to supply the particle accelerator with a plurality of voltage pulses, wherein the particle accelerator is operable to accelerate the charged particles based on the plurality of voltage pulses, and to produce an output beam comprising one or more radiation pulses for flash radiotherapy, wherein:
   the photoconductive switch is configured to receive light from a light source and to operate in response to the received light, the photoconductive switch being operable in a linear mode of operation in response to the received light, the photoconductive switch includes a doped crystalline material that is configured to receive a voltage from an energy source to establish an electric field across the crystalline material, and the photoconductive switch is operable to modify one or more of an amplitude, shape, spacing, number or width of the plurality of voltage pulses supplied to the particle accelerator.

2. The accelerator system of claim 1, wherein the photoconductive switch is operable to modify an energy, instantaneous dose rate or average dose rate of the one or more radiation pulses of the output beam based on modification of the one or more of amplitude, shape, spacing, number or width of the plurality of voltage pulses supplied to the particle accelerator.

3. The accelerator system of claim 1, wherein:
the photoconductive switch is configured to receive feedback information associated with a measurement of the one or more radiation pulses of the output beam, and
the photoconductive switch is operable to modify the one or more of amplitude, shape, spacing, number or width of the plurality of voltage pulses based on the feedback information.

4. The accelerator system of claim 3, further comprising a radiation measurement device configured to conduct the measurement of the one or more radiation pulses of the output beam.

5. The accelerator system of claim 1, wherein the accelerator system has a three-dimensional footprint of less than or equal to 100 cubic meters.

6. The accelerator system of claim 1, wherein the accelerator system is operable to:

produce the one or more radiation pulses of the output beam with an instantaneous dose rate that exceeds $1.8 \times 10^5$ Gy/s, administer a totality of the one or more radiation pulses of the output beam that constitute a required dose in less than 200 ms, produce the one or more radiation pulses of the output beam with an average dose rate between 40-100 Gy/s, and irradiate an entirety of a target region with levels above both the instantaneous and average dose rates.

7. The accelerator system of claim 1, wherein one or more of the plurality of voltage pulses has a non-Gaussian profile.

8. The accelerator system of claim 7, wherein the one or more of the plurality of voltage pulses has a top hat profile.

9. The accelerator system of claim 1, wherein the particle accelerator is an induction linear accelerator.

10. The accelerator system of claim 1, comprising the light source, wherein the light source includes one or more laser sources.

11. The accelerator system of claim 1, comprising the energy source, wherein the energy source is coupled to the photoconductive switch.

12. The accelerator system of claim 11, wherein the energy source comprises one or more capacitors.

13. The accelerator system of claim 11, wherein the energy source comprises a voltage source that is coupled to a first and a second electrode of the photoconductive switch.

14. The accelerator system of claim 1, wherein the charged particles comprise electrons.

15. The accelerator system of claim 1, wherein the particle accelerator includes a beam pipe that accommodates multiple charged particle beams therein.

* * * * *